(12) United States Patent
Lin et al.

(10) Patent No.: US 12,023,310 B2
(45) Date of Patent: Jul. 2, 2024

(54) METHOD FOR TREATING PERIPHERAL NERVE SHEATH TUMOR

(71) Applicant: GONGWIN BIOPHARM CO., LTD, Taipei (TW)

(72) Inventors: Mao-Yuan Lin, Taipei (TW); Chuan-Ching Yang, Taipei (TW); Nan-Shan Zhong, Guangzhou (CN)

(73) Assignee: GONGWIN BIOPHARM CO., LTD, Taipei (TW)

( * ) Notice: Subject to any disclaimer, the term of this patent is extended or adjusted under 35 U.S.C. 154(b) by 0 days.

(21) Appl. No.: 17/300,319

(22) Filed: Aug. 30, 2022

(65) Prior Publication Data

US 2024/0082182 A1    Mar. 14, 2024

(51) Int. Cl.
*A61K 31/18* (2006.01)
*A61K 47/10* (2017.01)
*A61P 35/00* (2006.01)

(52) U.S. Cl.
CPC ............... *A61K 31/18* (2013.01); *A61K 47/10* (2013.01); *A61P 35/00* (2018.01)

(58) Field of Classification Search
CPC .......... A61K 31/18; A61K 47/10; A61P 35/00
See application file for complete search history.

(56) References Cited

U.S. PATENT DOCUMENTS

| | | | | |
|---|---|---|---|---|
| 8,101,799 B2 * | 1/2012 | Maderna | ............... | A61P 9/00 564/92 |
| 8,710,059 B2 * | 4/2014 | Haupt | ............... | C07D 243/08 514/255.03 |
| 8,980,897 B2 * | 3/2015 | Clary | ............... | C07D 213/68 514/253.01 |

OTHER PUBLICATIONS

Mooring et al. Benzenesulfonamides: A Unique Class of Chemokine Receptor Type 4 Inhibitors. ChemMedChem. 2013;8(4):622-632. (Year: 2013).*
Rawle et al. Oxazole-Benzenesulfonamide Derivatives Inhibit HIV-1 Reverse Transcriptase Interaction with Cellular eEF1A and Reduce Viral Replication. J Virol. 2019;93(12):e00239-19. Published May 29, 2019. (Year: 2019).*
Prudner et al. Diagnosis and management of malignant peripheral nerve sheath tumors: Current practice and future perspectives. Neurooncol Adv. 2019;2(Suppl 1):i40-i49. Published Nov. 14, 2019. (Year: 2019).*
Korfhage et al. teach. Malignant Peripheral Nerve Sheath Tumors: From Epigenome to Bedside. Mol Cancer Res. 2019;17(7):1417-1428. (Year: 2019).*
The Cleveland Clinic. Nerve Sheath Tumors, obtained from https://my.clevelandclinic.org/health/diseases/22526-nerve-sheath-tumors on Dec. 27, 2023. (Year: 2023).*
Staedtke et al. Cancer of the Peripheral Nerve in Neurofibromatosis Type 1. Neurotherapeutics. 2017;14(2):298-306. (Year: 2017).*

* cited by examiner

*Primary Examiner* — Matthew P Coughlin
*Assistant Examiner* — Ashli Ariana Chicks
(74) *Attorney, Agent, or Firm* — Hoxie & Associates LLC

(57) ABSTRACT

Provided is a pharmaceutical composition for treating malignant peripheral nerve sheath (MPNST), including a benzenesulfonamide derivative and a pharmaceutically acceptable carrier. Also provided is a method for treating canine MPNST by administering the pharmaceutical composition to a subject in need thereof.

15 Claims, 4 Drawing Sheets
(1 of 4 Drawing Sheet(s) Filed in Color)

| 01-S10-E10 | T1 | T2 | RV | T3 | T4 | T5 | T6 | CV |
|---|---|---|---|---|---|---|---|---|
| Date | 10/29/21 | 11/2/21 | 11/5/21 | 11/9/21 | 11/12/21 | 11/19/21 | 11/30/21 | 12/14/21 |
| Day after treatment | 1 | 5 | 8 | 12 | 15 | 22 | 33 | -- |
| Body temperature (before treatment) | 38.20 | 37.60 | 38.10 | 37.40 | 37.80 | 38.3 | 37.30 | -- |
| Body temperature (after treatment) | 37.90 | 37.00 | -- | 37.7 | 37.5 | 38.10 | 38.10 | -- |
| Weight change | -0.79 | -1.60 | -- | 0.80 | -0.79 | -0.52 | 2.14 | -- |

METHOD FOR TREATING PERIPHERAL NERVE SHEATH TUMOR

BACKGROUND

1. Technical Field

The present disclosure relates to methods for treating peripheral nerve sheath tumor (PNST), and particularly to methods for treating malignant peripheral nerve sheath tumor (MPNST).

2. Description of Related Art

Peripheral nerve sheath tumor (PNST), endoneurial fibroblasts, and/or Schwann cells occurs relatively infrequently in animals except dog. It is classified as benign and malignant tumor. Malignant PNSTs (MPNSTs) arise most commonly from peripheral nerves, spinal roots, and cranial nerves in dogs. MPNSTs occur in middle-aged to older dogs, particularly in medium- to large-breeds and are characterized by slow growth and rare metastasis.

Canine PNSTs resemble malignant PNSTs in humans, regarding both histology and behavior. Histologically, the PNST is characterized by interacting patterns of spindle cells. There are two histological patterns including Antoni types A and B, which are dense areas of spindle shaped cells and less cellular areas with more pleomorphic cells, respectively. This kind of tumor spreads proximally and distally along the nerve and may ultimately involve the spinal cord, causing compression and associated neurological deficits. Despite metastases are rare, lung and uveal metastases have been reported.

There are therapeutic options for MPNST including surgical resection, radiotherapy, and chemotherapy. Early detection of the mass and correct diagnosis is the core of this tumor for complete surgical resection and postsurgical radiotherapy could reduce local recurrences. Recommended chemotherapeutic method is a combination of vincristine, doxorubicin, and cyclophosphamide. However, it has not yet been sufficiently researched. The novel therapy of mertonomic therapy has recently become one of the therapeutic options.

Nevertheless, there is still lacking optimization of proper drugs, dose, and schedule for the treatment of MPNST. In view of the high incidence of MPNST with serious health threats, it is an urgent and unmet need to develop pharmaceutical compositions to break through the current technical limitations and meet demands in effective treatment of MPNST.

BRIEF SUMMARY

In view of the foregoing, the present disclosure provides effective and safe pharmaceutical compositions that can be used for the treatment or adjuvant treatment of MPNST. The pharmaceutical composition comprises a benzenesulfonamide derivative and a pharmaceutically acceptable carrier thereof. By administration of the pharmaceutical composition provided in the present disclosure, the size of tumor in the subject is reduced and the life quality thereof can be improved.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present disclosure can be more fully understood by reading the following descriptions of the embodiments, with reference made to the accompanying drawings.

DETAILED DESCRIPTION

Figure 1:
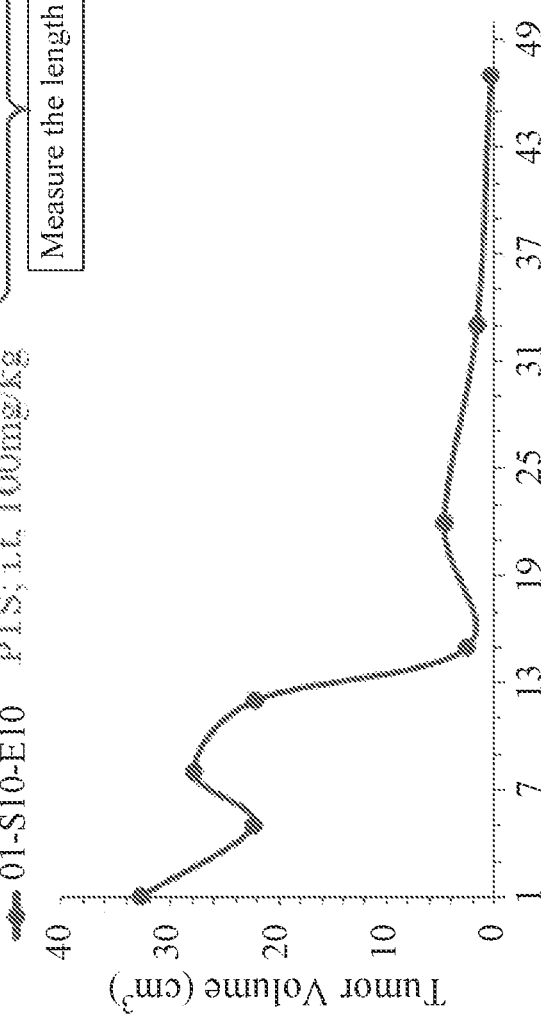
FIG. 1 shows the volume change of MPNSTs in the tumor of the dog (Case No. 01-S10-E10) treated with the GW-MP101 drug, wherein the dosage of PTS in the GW-MP101 drug is 100 mg/kg/dog. PTS: para-toluene sulfonamide; i.t: intratumoral administration.

The following examples are used to exemplify the present disclosure. A person of ordinary skill in the art can understand the other advantages of the present disclosure, based on the specification of the present disclosure. The present disclosure can also be implemented or applied as described in different examples. It is possible to modify and/or alter the following examples for carrying out this disclosure without contravening its scope for different aspects and applications.

It is noted that, as used in this disclosure, the singular forms "a," "an," and "the" include plural referents unless expressly and unequivocally limited to one referent. The term "or" is used interchangeably with the term "and/or" unless the context clearly indicates otherwise.

As used herein, the term "comprise," "comprising," "include," "including," "have," "having," "contain," "containing," and any other variations thereof are intended to cover a non-exclusive inclusion. For example, when describing an object "comprises" a limitation, unless otherwise specified, it may additionally include other ingredients, elements, components, structures, regions, parts, devices, systems, steps, or connections, etc., and should not exclude other limitations.

As used herein, the terms "at least one" and "one or more" may have the same meaning and include one, two, three, or more.

Throughout this disclosure, ordinal numbers (e.g., first, second, third, etc.) may be used as an adjective for an element (i.e., any noun in the application). The use of ordinal numbers is not to imply or create an ordering of the elements nor to limit any element to being only a single element unless expressly indicated, such as by the use of the terms "before," "after," "single," and other such terminology. Rather, the use of ordinal numbers is to distinguish between the elements. By way of an example, a first element is distinct from a second element, and the first element may encompass more than one element and succeed (or precede) the second element in an ordering of elements.

As used herein, the term "about" generally means within ±20%, ±10%, ±5%, ±1% ±0.5%, ±0.1% of a given value or range. Alternatively, the term "about" means within an acceptable standard error of the mean when considered by one of ordinary skill in the art. Unless otherwise expressly specified, all of the numerical ranges, amounts, values and percentages such as those for quantities of materials, durations of time periods, temperatures, operating conditions, ratios of amounts, and the likes disclosed herein should be understood as modified in all instances by the term "about." Such variations in the numerical value may occur by, e.g., the experimental error, the typical error in measuring or handling procedure for making compounds, compositions, concentrates, or formulations, the differences in the source, manufacture, or purity of starting materials or ingredients used in the present disclosure, or like considerations.

The numeral ranges used herein are inclusive and combinable, any numeral value that falls within the numeral scope herein could be taken as a maximum or minimum value to derive the sub-ranges therefrom. For example, it should be understood that the numeral range "1% to 50%" comprises any sub-ranges between the minimum value of 1% to the maximum value of 50%, such as the sub-ranges from 1% to 20%, from 30% to 50%, and from 15% to 45%. In addition, a plurality of numeral values used herein can be optionally selected as maximum and minimum values to derive numerical ranges. For instance, the numerical ranges of 10% to 25%, 10% to 50%, and 25% to 50% can be derived from the numeral values of 10%, 25%, and 50%.

As used herein, the term "treat," "treating" or "treatment" encompasses partially or completely ameliorating, mitigating and/or managing a symptom, a disorder or a condition associated with a disease. The term "treat," "treating" or "treatment" as used herein refers to application or administration of one or more therapeutic agent or surgery to a subject, who has a symptom, a disorder or a condition associated with a disease, with the purpose to partially or completely alleviate, ameliorate, relieve, delay onset of, inhibit progression of, reduce severity of, and/or reduce incidence of one or more symptoms, disorders or conditions associated with the disease. Treatment may be administered to a subject who exhibits only an early sign of such symptoms, disorders, and/or conditions for the purpose of decreasing the risk of developing the symptoms, disorders, and/or conditions associated with a disease.

As used herein, the terms "subject," "individual" and "patient" may be interchangeable and refer to an animal, e.g., a mammal. The term "subject" is intended to refer to both the male and female gender unless one gender is specifically indicated. At least on embodiment of the present disclosure, the subject is selected from the group consisting of a rodent, a murine, a monkey, a guinea pig, a dog, a cat, a cow, a sheep, a pig, a horse, a rabbit, and a human. In some preferable embodiments, the subject is a dog or a cat. In some preferable embodiments, the subject is a human.

As used herein, the term "substituted," when used to describe a chemical structure or moiety, refers to a derivative of that structure or moiety, wherein one or more of its hydrogen atoms is/are substituted with one or more substituent(s). Unless otherwise indicated, a "substituted" structure or moiety has a substituent at one or more substitutable positions of the structure or moiety, and when more than one position in any given structure or moiety is substituted, the substituent is either the same or different at each position.

The present disclosure is directed to a pharmaceutical composition for treating MPNST in a subject in need thereof, comprising a benzenesulfonamide derivative in a therapeutically effective amount and a pharmaceutically acceptable carrier thereof. The present disclosure is further directed to a method for treating MPNST, comprising administering a therapeutically effective amount of the pharmaceutical composition of the present disclosure to the subject in need thereof.

In at least one embodiment of the present disclosure, the benzenesulfonamide derivative is represented by formula (I) below:

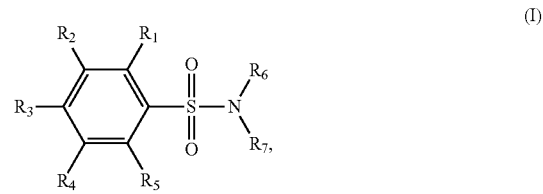

or a pharmaceutically acceptable salt thereof,
wherein $R_1$ to $R_7$ are independently selected from the group consisting of H, a $C_1$-$C_6$ linear or branched alkyl group, a $C_1$-$C_6$ linear or branched alkoxy group, a $C_3$-$C_6$ cycloalkyl group, a $C_3$-$C_6$ cycloheteroalkyl group, an amino group, and a halo group, or $R_6$ and $R_7$ are linked to each other to form a ring.

In at least one embodiment of the present disclosure, the alkyl group, the alkoxy group, the cycloalkyl group, the cycloheteroalkyl group, and the ring in $R_1$ to $R_7$ are independently unsubstituted or substituted with one or more substituents. In some embodiments of the present disclosure, the substituent is selected from the group consisting of phenyl, halo, oxo, ether, hydroxyl, carboxyl, amino, sulfo, and sulfonamide group.

In at least one embodiment of the present disclosure, the benzenesulfonamide derivative may be, but not limited to, para-toluene sulfonamide (p-TSA), ortho-toluene sulfonamide, meta-toluene sulfonamide, N-ethyl-ortho-toluene sulfonamide, N-ethyl-para-toluene sulfonamide, or N-cyclohexyl-para-toluene sulfonamide.

In at least one embodiment of the present disclosure, the benzenesulfonamide derivative is at least one of para-toluene sulfonamide, ortho-toluene sulfonamide, and meta-toluene sulfonamide. The monomer of the benzenesulfonamide derivative is in the form of white crystal. In some embodiments, the pharmaceutical composition comprises a combination of two or more different benzenesulfonamide derivatives in any ratio.

In at least one embodiment of the present disclosure, the pharmaceutically acceptable carrier contained in the pharmaceutical composition of the present disclosure may be at least one selected from the group consisting of a filler, a binder, a preservative, a disintegrating agent, a lubricant, a suspending agent, a wetting agent, a biocompatible solvent, a penetration enhancer, a surfactant, a thickening agent, an acid, a flavoring agent, a complexing agent, and any combination thereof.

In at least one embodiment of the present disclosure, the pharmaceutically acceptable carrier contained in the pharmaceutical composition of the present disclosure may be at least one selected from the group consisting of alkylene glycol, sebacic acid, dimethyl sulfoxide, ethanol, and any combination thereof.

In at least one embodiment of the present disclosure, the examples of the binder include, but are not limited to, paste, sorbitol, guar gum, polyvinyl pyrrolidone, cellulose derivatives, such as hydroxypropyl methylcellulose, carboxymethyl cellulose, carbomer (commercially available as Carbopols), and any combination thereof.

In at least one embodiment of the present disclosure, the examples of the preservative include, but are not limited to, sodium benzoate, methyl paraben, propyl paraben, cresol, and any combination thereof.

In at least one embodiment of the present disclosure, the examples of the lubricant include, but are not limited to, metal stearates (such as magnesium stearate, calcium stearate, and sodium stearate), stearic acid, talc, polyethylene glycol, soluble salts (such as sodium chloride and sodium benzoate), and any combination thereof.

In at least one embodiment of the present disclosure, the examples of the wetting agent include, but are not limited to, glycerin, sorbitol, polypropylene glycol, and any combination thereof.

In at least one embodiment of the present disclosure, the examples of the flavoring agent include, but are not limited to, peppermint oil, menthol, lemon oil, orange oil, cinnamon oil, and any combination thereof.

In at least one embodiment of the present disclosure, the pharmaceutically acceptable carrier may be polyethylene glycol (PEG), alkylene glycol, propylene glycol, sebacic acid, dimethyl sulfoxide (DMSO), ethanol, or any combination thereof. In some embodiments, the examples of the alkylene glycol include, but are not limited to, polyethylene glycol, propylene glycol, hexylene glycol, and any combination thereof.

In at least one embodiment of the present disclosure, the pharmaceutically acceptable carrier is chosen from at least one of 1% to 50% by weight of polyethylene glycol 400, 1% to 10% by weight of 1,2-propylene glycol, 1% to 10% by weight of sebacic acid, 1% to 20% by weight of 2-ethyl-1, 3-hexanediol, 0% to 20% by weight of dimethyl sulfoxide, and 0% to 20% by weight of ethanol.

In at least one embodiment of the present disclosure, the benzenesulfonamide derivative is present in an amount of from 1% to 60% of the pharmaceutical composition by weight, such as about 1%, 2%, 5%, 10%, 15%, 20%, 25%, 30%, 33%, 35%, 40%, 45%, 50%, 53%, 55% and 60%. In some embodiments, an amount of the benzenesulfonamide derivative in the pharmaceutical composition has a lower limit chosen from about 1%, 5%, 10%, 15%, 20%, and 25% of the composition by weight, and an upper limit chosen from about 60%, 55%, 50%, 45%, 40%, and 35% of the composition by weight. In some embodiments, the benzenesulfonamide derivative is present in an amount of from 20% to 40% of the composition by weight.

In at least one embodiment of the present disclosure, the pharmaceutical composition GW-MP101 provided herein comprises 1% to 50% by weight of para-toluene sulfonamide, 1% to 40% by weight of PEG 400, 4% to 10% by weight of 1,2-propylene glycol, 1% to 5% by weight of sebacic acid, 0% to 15% by weight of para-toluene sulfonic acid, 1% to 20% by weight of 2-ethyl-1,3-hexanediol, 0% to 10% by weight of dimethyl sulfoxide, and 0% to 20% by weight of ethanol.

In at least one embodiment of the present disclosure, the pharmaceutical composition comprises at least one of 10% to 40% by weight of polyethylene glycol 400, 1% to 10% by weight of 1,2-propylene glycol, 1% to 5% by weight of sebacic acid, 10% to 20% by weight of 2-ethyl-1,3-hexanediol, 0% to 40% by weight of dimethyl sulfoxide, and 0% to 20% by weight of ethanol The process for preparing an injection formulation of the GW-MP101 preparation can be carried out by, for example, adding an adjuvant and/or a solvent to adjust the mixture to be isotonic. Further, the step of filtering in the process can be carried out by, for example, using a microporous filter.

In at least one embodiment of the present disclosure, the pharmaceutical composition may be formulated into a form suitable for the following administration routes: enteral administration, sublingual administration, subcutaneous administration, rectal administration, and parenteral administration, such as subcutaneous injection, intramuscular injection, intravenous injection, intratumoral injection, abdominal injection, intraarterial injection, and subarachnoid injection. In some embodiments of the present disclosure, the pharmaceutical composition may be in a form selected from the group consisting of an injection formulation, a dry powder, a tablet, an oral liquid, a flake, a film, a lozenge, a capsule, a granule, a pill, a gel, a lotion, an ointment, an emulsifier, a paste, a cream, an eye drop, and a salve.

In at least one embodiment of the present disclosure, the pharmaceutical composition may be administered to the subject intratumorally, intravenously, subcutaneously, intradermally, orally, intrathecally, intraperitoneally, intranasally, intramuscularly, intrapleurally, topically, or through nebulization.

In at least one embodiment of the present disclosure, the pharmaceutical composition may be used to treat a canine MPNST by triggering ablation of the MPNST. For example, the GW-MP101 preparation of the present disclosure for triggering ablation of the canine MPNST may be in the form of an injection formulation and administered to the subject by intratumoral injection. The intratumoral injection dose for canine MPNST ablation may be from 0.1 mL/injection to 5 mL/injection (about 33 mg to 1650 mg of para-toluene sulfonamide or other benzenesulfonamide derivatives).

As used herein, the phrase "a therapeutically effective amount" refers to the amount of an active ingredient (e.g., the benzenesulfonamide derivative) that is required to confer a desired therapeutic effect (e.g., triggering ablation of a canine MPNST) on the treated subject. Effective doses will vary, as recognized by one of ordinary skill in the art, depending on routes of administration, excipient usage, the possibility of co-usage with other therapeutic treatment, and the condition to be treated.

In at least one embodiment of the present disclosure, the benzenesulfonamide derivative may be administered to the subject in a therapeutically effective amount of from about 1 mg/day to about 2000 mg/day during a treatment period or a treatment cycle, such as 10 mg/day to 450 mg/day, 30 mg/day to 200 mg/day, or 40 mg/day to 150 mg/day. As used herein, the term "treatment cycle" refers to a treatment period followed by a rest period without treatment that is repeated on a regular schedule.

In some embodiments of the present disclosure, the injection dosage for treating canine MPNST may be in a range of from about 0.5 mg/day to 950 mg/day, from 1 mg/day to 900 mg/day, from 3 mg/day to 800 mg/day, from 5 mg/day to 750 mg/day, from 8 mg/day to 700 mg/day, from 10 mg/day to 650 mg/day, from 15 mg/day to 600 mg/day, from 25 mg/day to 550 mg/day, from 35 mg/day to 500 mg/day, from 45 mg/day to 450 mg/day, from 50 mg/day to 400 mg/day, from 55 mg/day to 350 mg/day, from 60 mg/day to 300 mg/day, and from 65 mg/day to 250 mg/day of p-toluenesulfonamide or other benzenesulfonamide derivatives.

In some embodiment of the present disclosure, the dosage of intratumoral injection for the ablation of MPNST is 19.4 mL to 50 mL about 6,400 mg to 16,500 mg of p-toluenesulfonamide or other benzenesulfonamide derivatives.

In at least one embodiment of the present disclosure, the pharmaceutical composition may be administered to the subject 1 to 2 times per day, 1 to 7 times per week, or 1 to 14 times per month. In at least one embodiment of the present disclosure, the pharmaceutical composition may be administered to the subject for a 1- to 4-week or 1- to 4-month treatment period or treatment cycle. In some embodiments, the pharmaceutical composition may be administered to the subject 2 to 3 times per week for a 2-week treatment period. In some embodiments, the pharmaceutical composition is administered to the subject equal to or more than 6 times in the first treatment period.

In at least one embodiment of the present disclosure, the pharmaceutical composition can be directly injected into MPNST or injected into the area surrounding the MPNST. In some embodiments of the present disclosure, the dosage can be proportionally increased or decreased according to a therapeutic situation. In at least one embodiment of the present disclosure, the administration may continue until the tumor shrinks about 5%, 10%, 15%, 20%, 25%, 30%, 35%, 40%, 45%, 50%, 55%, 60%, 65%, 70%, 75%, 80%, 85%, 90%, or 95% (by volume or weight), or until the tumor is fully eliminated.

The present disclosure also provides a use of a pharmaceutical composition in the manufacture of a medicament for treating a canine MPNST, wherein the pharmaceutical composition comprises a benzenesulfonamide derivative of the present disclosure and a pharmaceutically acceptable carrier thereof.

The present disclosure also provides a use of a pharmaceutical composition in the manufacture of a medicament for treating MPNST, and the pharmaceutical composition comprises the benzenesulfonamide derivative and the pharmaceutically acceptable carrier thereof as mentioned above. The present disclosure further provides the pharmaceutical composition for use in the treatment of MPNST, and the pharmaceutical composition comprises the benzenesulfonamide derivative and the pharmaceutically acceptable carrier thereof as mentioned above.

The following embodiments further demonstrate the efficacy of the current disclosure, but should not be used to limit the scope of the present disclosure.

EXAMPLES

The present disclosure is further described by means of the following examples. However, these examples are only illustrative of the disclosure, and in no way limit the scope and meaning of the present disclosure. Indeed, many modifications and variations of the present disclosure will be apparent to those skilled in the art upon reading this specification, and can be made without departing from its scope.

Preparation Example

The pharmaceutical composition GW-MP101 for intratumoral injection administration was a clear, colorless, oily, sterile solution, containing the components as listed in Table 1, and that could be packaged in 5 mL glass ampoules. GW-MP101 contains 330 mg/mL of the active drug p-TSA.

TABLE 1

| p-Toluenesulfonamide | 1%-60% |
| PEG-400 | 10%-40% |
| 1,2-Propylene glycol | 1%-10% |
| Sebacic acid | 1%-5% |

TABLE 1-continued

| p-Toluenesulfonic acid | 0%-5% |
| 2-Ethyl-1,3-hexanediol | 10%-20% |
| Dimethyl sulfoxide | 0-40% |
| Ethanol | 0-20% |

Preparation of the composition of the present disclosure includes the process of: adding and mixing the solvents and adjuvants in a given ratio; heating the mixture to 80° C. to 110° C. with stirring to form a clear oily liquid; gradually adding the sulfa drug with stirring until completely dissolved; filtering and cooling the mixture to obtain the composition of the present disclosure in an oily liquid form GW-MP101.

The preparation of the GW-MP101 injection may be conducted by some techniques known in the art, e.g., adding an adjuvant and/or solvent to adjust the mixture to an isotonic state, or filtering the mixture by using a microporous filter.

The present disclosure also provides the use of GW-MP101 as a medicament for promoting tumor ablation in the body of the subject.

The efficacy of the tumor disclosed in the present disclosure was assessed by the following veterinary clinical trials. The trials followed the relevant ethical principles of Veterinary Good Clinical Practice.

Embodiment 1

The case in the clinical trial was carried out at Evergreen animal hospital in Taipei city, Taiwan from October to December 2021.

Dog breed: Corgi
Gender: Male
Age: 13 years old
Weight: 11 kg to 12 kg
Liver function: normal
Kidney function: normal
Pathology: Malignant peripheral nerve sheath tumor, grade 2
Medical history: Anemia The inclusion criteria are: (A) the dog is greater than or equal to 1 year old; (B) the dog is diagnosed with MPNST by cytology or histopathology; (C) the trial veterinarian assesses that the dog is unsuitable for removal of the tumor by surgery; (D) the dog has at least one measurable tumor that is larger than 1 cm in diameter; (E) the trial veterinarian assesses the life expectancy of the dog to exceed 3 months; and (F) the owner can understand and abide by the experimental procedure and is willing to sign an informed consent form.

The exclusion criteria are: (A) the dog has received systemic chemotherapy within 4 weeks before entering the trial; (B) the dog has received radiotherapy within 4 weeks before entering the trial; (C) the dog has underwent a major operation (for example, thoracotomy is not allowed, but the non-invasive operation, such as biopsy, is allowed) within 4 weeks before entering the trial; (D) the dog is treated by any other experimental drugs, biological formulations, medical materials, or other anti-tumor treatments (such as immunomodulators and radiotherapy) within 4 weeks before entering this trial or during the period of this trial experiment; (E) the dog has the following abnormal value of blood tests before entering the trial: a. hemoglobin<6.0 g/dL; b. absolute neutrophil count (ANC)<1,500/μL; c. albumin<1.5 g/dL; d. total bilirubin<2 mg/dL; e. alanine aminotransferase (ALT) and aspartate aminotransferase (AST)>5× upper normal limit (UNL); f. chronic kidney disease (CKD), the International Renal Interest Society (IRIS)>stage 3; (F) the dog suffers from any other serious diseases such as infection, uncontrolled diabetes, stage C of chronic degenerative valve disease (CDVD, one of the heart diseases), gastric ulcer, severe autoimmune disease, and the trial veterinarian restricts the animal from participating in this trial after assessment; (G) the dog is known or suspected of having allergic reactions to the ingredients contained in any p-toluenesulfonamide drugs; (H) the trial veterinarian diagnoses that the dog's tumor was blocked by important blood vessels, so it is difficult to perform intratumoral injection therein; (I) the dog is pregnant; and (J) the trial veterinarian determines that the dog is unsuitable for participating in this trial.

Those who met at least one of the following criteria should be withdrawn from clinical trials: (A) the informed consent form is withdrawn; (B) the dog receives the treatment prohibited by this trial; (C) after assessing any pathological characteristics, clinical adverse events, or any changes in the condition of the animal, the trial veterinarian determines that it is not the most advantageous situation to allow the dog to continue participating in the trial; (D) the dog is pregnant during the treatment period or is suspected of being pregnant by its owner or the trial veterinarian; (E) the dog has an adverse event of grade 3 or above according to international adverse events of oncology organization (Veterinary Cooperative Oncology Group—Common Terminology Criteria for Adverse Events, VCOG-CTCAE) and cannot return to grade 1 within 7 days after the adverse event, or the grade 3 or above adverse event still occurs after 2 dose reductions in the dog; (F) signs and symptoms of disease progression or deterioration (assessment of deterioration was based on Veterinary Cooperative Oncology Group—Response Evaluation Criteria in Solid Tumors v1.0 (VCOG-RECIST v1.0)); (G) death; (H) loss of follow-up tracking; and (I) violation of the plan.

Treatment Method:

The test dog was given intratumoral injections of 3.8, 3.7, 1, 3.7, 3.6, 3.6 mL of the GW-MP101 drug on Day 1, 5, 8, 12, 15, 22, 33, 47 (each time about 1180 to 1250 mg of p-toluenesulfonamide). The injections were carried out in single, multi-point (2 to 10 points) intratumoral injections.

Response Assessment Criteria:

The electronic vernier caliper measurement was performed before each administration, and the computed tomography (CT) scan was performed before the first administration and at the conclusion visit. Complete response (CR) means that a measurable or evaluable tumor disappears completely, and no new tumors appear for more than four weeks. Partial response (PR) means that a measurable or evaluable tumor shrinks by more than or equal to 30%, and no new tumors appear for more than four weeks. Stable disease (SD) means that a measurable or evaluable tumor shrinks by less than or equal to 30% or enlarges by less than or equal to 20%. Disease progression (PD) means that a measurable or evaluable tumor enlarges by more than or equal to 20%, or other tumors deteriorate, and new tumors appear.

Safety Assessment:

When conducting safety assessment during the trial period, the relevant researchers of the trial were responsible for defining and compiling the adverse events in the protocol (the method for assessment was referred to "Veterinary Cooperative Oncology Group-Common Terminology Criteria for Adverse Events (VCOG-CTCAE)."

The followings show the treatment results of MPNST in Embodiment 1.

Tumor Volume Change (Measured with the Electronic Vernier Caliper):

Regarding the tumor, the measurement range thereof was located in the MPNST of the right limb of the dog. After 6 times administrations of the GW-MP101 drug, the volume of the tumor changed. The volume of the tumor was 32.84 cm$^3$ before treatment, 22.37 cm$^3$ before the 2nd administration, and 0.30 cm$^3$ at the assessment visit (6 weeks after the 2nd administration). Comparing the volume of the tumor before the first administration with that at the assessment visit, the measurable or assessable tumor shrinks by 100%, and the result was a complete response (CR) (referring to Table 1 below and FIG. 1).

TABLE 1

|  | D1<br>T1 | D5<br>T2 | D8<br>RV | D12<br>T3 | D15<br>T4 | D22<br>T5 | D33<br>T6 | D47<br>CV |
|---|---|---|---|---|---|---|---|---|
| a | 3.89 | 3.45 | 3.65 | 3.20 | 2.59 | 2.07 | 1.38 | 0.59 |
| b | 4.47 | 4.09 | 4.20 | 3.74 | 2.70 | 2.39 | 1.13 | 0.52 |
| c | 3.78 | 3.17 | 3.65 | 3.71 | 0.73 | — | — | — |
| Volume | 32.84 | 22.37 | 27.88 | 22.23 | 2.53 | 4.60 | 1.56 | 0.30 |

Volume (cm$^3$)=a (cm)×b (cm)×c (cm)×½

Figure 2:
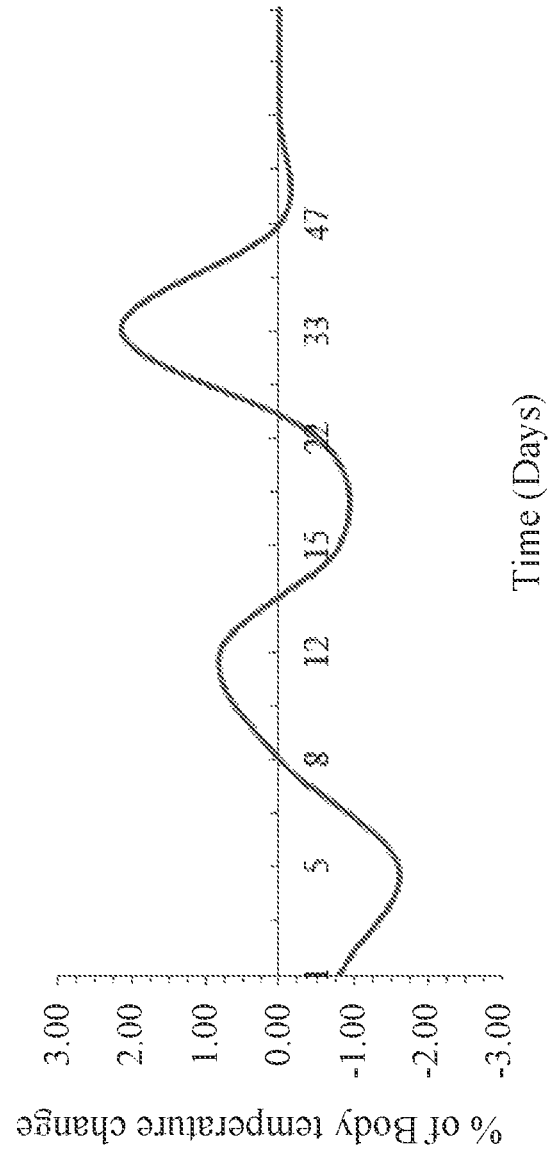
FIG. 2 shows the body temperature change of the dog (Case No. 01-S10-E10) treated with the GW-MP101 drug, wherein the dosage of PTS in the GW-MP101 drug is 100 mg/kg/dog. PTS: para-toluene sulfonamide; i.t: intratumoral administration.

D: Day; T1 to T6: the 1st to 6th administration of treatment; RV: Random Visit; CV: Conclusion Visit Body Temperature Change:

The variation of the body temperature before and after each treatment is within 2.5 degree. (referring to Table 2 below and FIG. 2).

TABLE 2

|  | D1<br>T1 | D5<br>T2 | D8<br>RV | D12<br>T3 | D15<br>T4 | D22<br>T5 | D33<br>T6 | D47<br>CV |
|---|---|---|---|---|---|---|---|---|
| Body temperature Before treatment | 38.20 | 37.60 | 38.10 | 37.40 | 37.80 | 38.30 | 37.30 | — |
| Body temperature After treatment | 37.90 | 37.00 | — | 37.7 | 37.5 | 38.10 | 38.10 | — |
| Change in body temperature | −0.79 | −1.60 | — | 0.80 | −0.79 | −0.52 | 2.14 | — |

Figure 3:
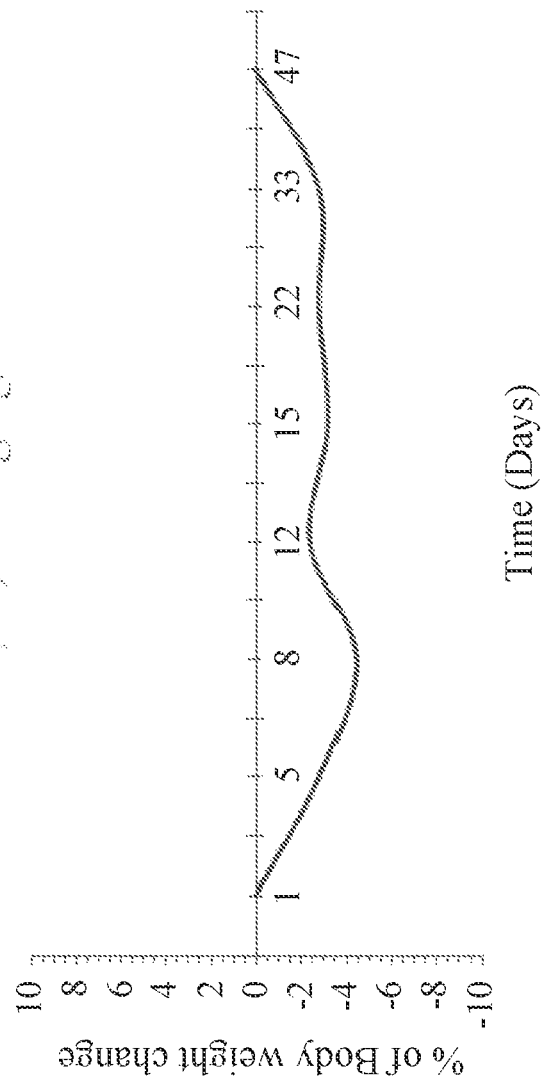
FIG. 3 shows the body weight change of the dog (Case No. 01-S10-E10) treated with the GW-MP101 drug, wherein the dosage of PTS in the GW-MP101 drug is 100 mg/kg/dog. PTS: para-toluene sulfonamide; i.t: intratumoral administration.

D: Day; T1 to T6: the 1st to 6th administration of treatment; RV: Random Visit; CV: Conclusion Visit Body Weight Change:

The variation of the body weight before and after each treatment is within 4.5 kilograms. (referring to Table 3 below and FIG. 3).

TABLE 3

|  | D1<br>T1 | D5<br>T2 | D8<br>RV | D12<br>T3 | D15<br>T4 | D22<br>T5 | D33<br>T6 | D47<br>CV |
|---|---|---|---|---|---|---|---|---|
| Body weight | 12.45 | 12.10 | 11.90 | 12.15 | 12.05 | 12.10 | 12.10 | — |
| Weight change | 0.00 | −2.81 | 4.42 | −2.41 | −3.21 | −2.81 | −2.81 | — |

Figure 4:
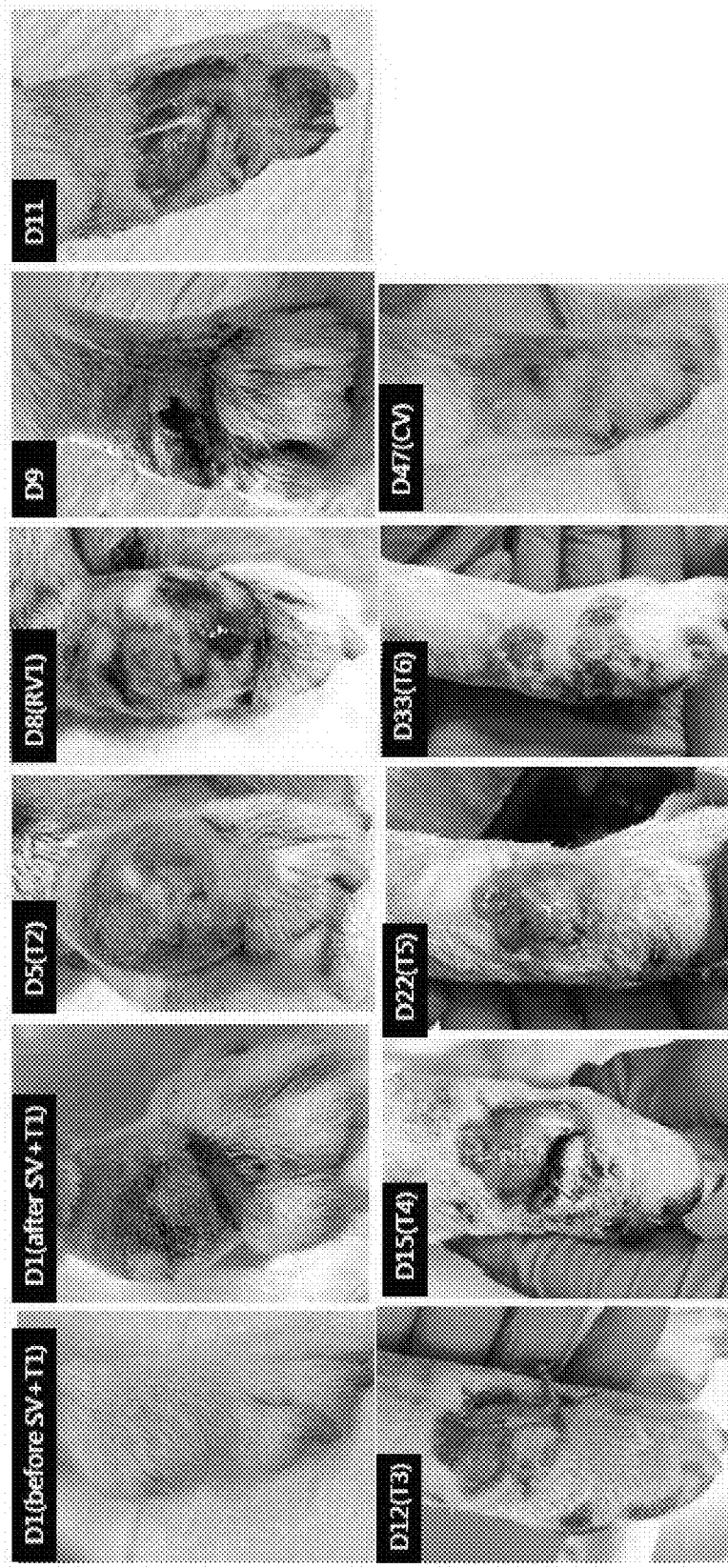
FIG. 4 shows the representative clinical photographs of canine MPNSTs in the tumor of the dog (Case No. 01-S10-E10) before and after the administration of the GW-MP101 drug. D: Day; T1 to T6: the 1st to 6th administration of the GW-MP101 drug; SV: Subject Visit; RV: Random Visit; CV: Conclusion Visit.

D: Day; T1 to T6: the 1st to 6th administration of treatment; RV: Random Visit; CV: Conclusion Visit Interim Efficacy (Appearance Change):

After 6 administrations of the GW-MP101 drug, an obvious change on the limb of the dog was observed, from being swollen to being flat at the tumor site (FIG. 4).

Adverse Effects:

No common side effects such as pain, nausea, vomiting or local redness and inflammation had been observed. The functions of liver and kidney were stable and normal during and after the treatment.

Conclusion of this Embodiment

The pharmaceutical composition of the present disclosure can effectively reduce or ablate tumor and thereby improve the quality of life and clinical symptoms of dogs with MPNST. Furthermore, no significant increase in adverse reactions has been observed in the clinical trials.

The disclosure has been described using exemplary embodiments. However, it is to be understood that the scope of the disclosure is not limited to the disclosed embodiments. On the contrary, it is intended to cover various modifications and similar rearrangement. The scope of the claims therefore should be accorded the broadest interpretation so as to encompass all such modifications and similar arrangements.

What is claimed is:

1. A method for treating a malignant peripheral nerve sheath, comprising administering a therapeutically effective amount of a pharmaceutical composition to a subject in need thereof, wherein the pharmaceutical composition comprises a benzenesulfonamide derivative and a pharmaceutically acceptable carrier thereof,
    wherein the benzenesulfonamide derivative is at least one selected from the group consisting of para-toluene sulfonamide, ortho-toluene sulfonamide, meta-toluene sulfonamide, N-ethyl-ortho-toluene sulfonamide, N-ethyl-para-toluene sulfonamide, N-cyclohexyl-para-toluene sulfonamide, and any combination thereof.

2. The method of claim 1, wherein the benzenesulfonamide derivative is para-toluene sulfonamide.

3. The method of claim 1, wherein the pharmaceutically acceptable carrier is at least one selected from the group consisting of a filler, a binder, a preservative, a disintegrating agent, a lubricant, a suspending agent, a wetting agent, a biocompatible solvent, a penetration enhancer, a surfactant, a thickening agent, an acid, a flavoring agent, a complexing agent, and any combination thereof.

4. The method of claim 1, wherein the pharmaceutically acceptable carrier is at least one selected from the group consisting of alkylene glycol, sebacic acid, dimethyl sulfoxide, ethanol, and any combination thereof.

5. The method of claim 4, wherein the alkylene glycol is at least one selected from the group consisting of polyethylene glycol, propylene glycol, hexylene glycol, and any combination thereof.

6. The method of claim 1, wherein the benzenesulfonamide derivative is present in an amount of from 1% to 50% by weight of the pharmaceutical composition.

7. The method of claim 6, wherein the benzenesulfonamide derivative is present in an amount of from 20% to 40% by weight of the pharmaceutical composition.

8. The method of claim 1, wherein the pharmaceutical composition further comprises at least one of 10% to 40% by weight of polyethylene glycol 400, 1% to 10% by weight of 1,2-propylene glycol, 1% to 5% by weight of sebacic acid, 10% to 20% by weight of 2-ethyl-1,3-hexanediol, 0% to 40% by weight of dimethyl sulfoxide, and 0% to 20% by weight of ethanol.

9. The method of claim 1, wherein the administering causes ablation of the malignant peripheral nerve sheath in the subject.

10. The method of claim 1, wherein the subject is selected from the group consisting of a rodent, a murine, a monkey, a guinea pig, a dog, a cat, a cow, a sheep, a pig, a horse, a rabbit, and a human.

11. The method of claim 10, wherein the subject is a dog or cat.

12. The method of claim 1, wherein the benzenesulfonamide derivative in the pharmaceutical composition is administered to the subject in the therapeutically effective amount of from about 10 mg/kg to about 100 mg/kg.

13. The method of claim 1, wherein the benzenesulfonamide derivative in the pharmaceutical composition is administered to the subject in the therapeutically effective amount of from about 10 mg/kg to about 5000 mg/kg during a treatment period or a treatment cycle.

14. The method of claim 1, wherein the pharmaceutical composition is administered to the subject intratumorally, intravenously, subcutaneously, intradermally, orally, intrathecally, intraperitoneally, intranasally, intramuscularly, intrapleurally, topically, or through nebulization.

15. The method of claim 1, wherein the pharmaceutical composition is in a form selected from the group consisting of an injection formulation, a dry powder, a tablet, an oral liquid, a flake, a film, a lozenge, a capsule, a granule, a pill, a gel, a lotion, an ointment, an emulsifier, a paste, a cream, an eye drop, and a salve.

* * * * *